United States Patent [19]

Leppard et al.

[11] Patent Number: 5,290,952
[45] Date of Patent: Mar. 1, 1994

[54] PHENYLTHIOPHENYL KETONES

[75] Inventors: David G. Leppard, Marly; Kurt Burdeska, Basel, both of Switzerland

[73] Assignee: Ciba-Geigy Corporation, Ardsley, N.Y.

[21] Appl. No.: 906,607

[22] Filed: Jun. 30, 1992

[30] Foreign Application Priority Data

Jul. 3, 1991 [CH] Switzerland ............ 1963/91-2

[51] Int. Cl.$^5$ .............. C07D 333/22; C07D 409/02; G03C 1/815
[52] U.S. Cl. .................. 549/72; 549/60; 430/512
[58] Field of Search ............... 549/72, 60

[56] References Cited

U.S. PATENT DOCUMENTS 3,785,827  1/1974  Piller et al. ................ 96/84

FOREIGN PATENT DOCUMENTS 1336942  7/1963  France .
973919  11/1964  United Kingdom .

Primary Examiner—Glennon H. Hollrah
Assistant Examiner—Deborah Lambkin
Attorney, Agent, or Firm—William A. Teoli, Jr.

[57] ABSTRACT

The novel compounds of formula

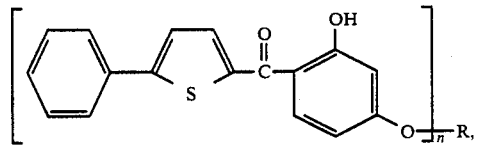

wherein n and R are as defined in claim 1, are very suitable for use as UV absorbers in layers of photographic materials.

5 Claims, No Drawings

PHENYLTHIOPHENYL KETONES

The present invention relates to novel phenylthiophenyl ketones and to the use thereof as UV absorbers in photographic materials, especially those with transparent supports.

The use of UV absorbers in photographic materials to reduce the harmful action of UV light on the material upon exposure is known. It is also known that UV absorbers help to render substantially ineffective the statics which occur during the production of photographic materials.

Phenylthiophenyl ketones of formula

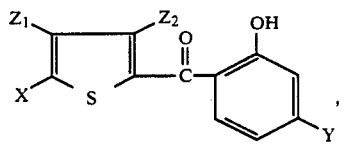
(A)

wherein $Z_1$ and $Z_2$ are hydrogen or alkyl, X is hydrogen, alkyl, phenyl or halophenyl, and Y is hydroxyl or an etherified hydroxyl group, are disclosed in GB-B-973 919. Their use in filter layers of photographic materials is mentioned.

It has been found, however, that the compounds disclosed in the above patent specification are too ineffective as UV absorbers and, because of their poor solubility in conventional solvents, can only be incorporated to a minor extent in photographic layers.

Novel compounds of the above type have now been found which can be more readily incorporated in photographic layers and which have enhanced activity as UV absorbers.

Accordingly, the invention provides compounds of formula

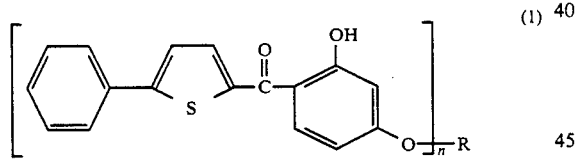
(1)

wherein n is 1, 2, 3 or 4, and

R, if n is 1, is alkyl of 1 to 18 carbon atoms or alkyl of 1 to 18 carbon atoms which is substituted by hydroxy; alkenoxy of 2 to 18 carbon atoms, halogen, phenoxy, —$CO_2H$, —$CO_2R_2$, —$CONH_2$, —$CONHR_3$, —$CONR_3R_4$, —$NH_2$, —$NHR_3$, —$NR_3R_4$, —$NHCOR_5$, —CN and/or —O—CO—$R_5$, or R is alkyl of 3 to 14 carbon atoms which is interrupted by oxygen, alkenyl of 3 to 6 carbon atoms, glycidyl, cyclohexyl, phenylalkyl containing 1 to 5 carbon atoms in the alkyl moiety, —$COR_6$, —$SO_2R_7$ or —$CH_2CH(OH)CH_2OR_1$, and $R_1$ is hydrogen, alkyl of 1 to 18 carbon atoms, cyclohexyl, benzyl, phenyl, tolyl, —CO—alkenyl containing 2 to 4 carbon atoms in the alkenyl moiety or glycidyloxyalkyl containing 3 to 14 carbon atoms in the alkyl moiety, $R_2$ is alkyl of 1 to 18 carbon atoms, alkyl or hydroxyalkyl, each of 3 to 14 carbon atoms and interrupted by oxygen, sulfur or —NH—, hydroxyalkyl of 2 to 18 carbon atoms, alkyl of 1 to 4 carbon atoms which is substituted by —$P(O)(OR_8)_2$, —$NR_3R_4$ or —O—$COR_5$, glycidyl, cycloalkyl of 5 to 12 carbon atoms, alkenyl of 3 to 18 carbon atoms, benzyl, phenyl, alkylphenyl containing 1 to 12 carbon atoms in the alkyl moiety, furfuryl or a radical of formula —$CH_2CH(OH)CH_2OR_1$, $R_3$ and $R_4$ are each independently of the other alkyl of 1 to 12 carbon atoms, alkoxyalkyl of 3 to 12 carbon atoms, dialkylaminoalkyl of 4 to 16 carbon atoms or cycloalkyl of 5 to 12 carbon atoms, or, when taken together, form an alkylene, oxaalkylene or azaalkylene radical, each containing 3 to 9 carbon atoms, $R_5$ is alkyl of 1 to 18 carbon atoms, alkenyl of 2 to 18 carbon atoms or phenyl, $R_6$ is alkyl of 1 to 18 carbon atoms, alkenyl of 2 to 18 carbon atoms or phenyl, alkoxy of 1 to 12 carbon atoms, phenoxy, alkylamino of 1 to 12 carbon atoms, phenylamino or naphthylamino, or a radical of formula —$R_9$—$CO_2H$ or —$NHR_{10}NCO$, $R_7$ is alkyl of 1 to 12 carbon atoms, phenyl, naphthyl or alkylphenyl containing 1 to 8 carbon atoms in the alkyl moiety, $R_8$ is alkyl of 1 to 12 carbon atoms or phenyl, $R_9$ is alkylene of 2 to 14 carbon atoms, vinylene or o-phenylene, and $R_{10}$ is alkylene of 2 to 10 carbon atoms, phenylene, tolylene or diphenylmethylene, or R, if n is 2, is alkylene of 2 to 16 carbon atoms, alkylene or hydroxyalkylene, each of 3 to 20 carbon atoms and interrupted by oxygen, hydroxyalkylene of 3 to 20 carbon atoms, alkenylene of 4 to 12 carbon atoms, xylylene or a radical of formula —$CH_2CH(OH)CH_2$—O—$R_{12}$—O—$CH_2CH(OH)CH_2$—, —CO—$R_{13}$CO—, —$CONHR_{13}NHCO$—, —$(CH_2)_mCO$—O—$R_{14}$—O—$CO(CH_2)_m$—, wherein m is 1, 2 or 3, or is

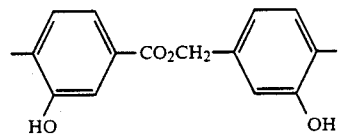

and $R_{12}$ is alkylene of 2 to 10 carbon atoms, alkylene of 3 to 14 carbon atoms which is interrupted by oxygen, phenylene or a radical of formula

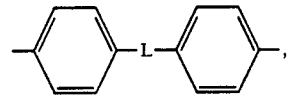

wherein L is —O—, —S—, —$SO_2$—, —$CH_2$— or —$C(CH_3)_2$—, $R_{13}$ is alkylene, oxalkylene or thiaalkylene, each of 2 to 10 carbon atoms, phenylene, napthylene or alkenylene of 2 to 6 carbon atoms, and $R_{14}$ is alkylene of 2 to 10 carbon atoms or alkylene of 4 to 30 carbon atoms which is interrupted by oxygen, or R, if n is 3, is a radical of formula

wherein m has the given meaning, and
$R_{15}$ is alkanetriyl of 3 to 12 carbon atoms, or
R, if n is 4, is a radical of formula

wherein m has the given meaning, and
$R_{16}$ is alkanetetrayl of 4 to 12 carbon atoms.

Further objects of the present invention are processes for the preparation of the compounds of formula (1) and photographic material which contains a layer in which such a compound is present.

In the above definitions, alkyl of 1 to 18 carbon atoms will typically be methyl, ethyl, propyl, butyl, pentyl, hexyl, heptyl, octyl, nonyl, decyl, undecyl, dodecyl, tetradecyl, hexadecyl and octadecyl and corresponding branched isomers.

Typical alkoxy radicals of 1 to 18 carbon atoms may be derived from the cited alkyl radicals. The same also applies to the alkenoxy radicals, which radicals may also be polyunsaturated, as well as to the alkylene radicals.

Exemplary of substituted alkyl radicals of 1 to 18 carbon atoms which may suitably be used in this invention are: $-CH_2CH_2OH$, $-CH_2CH(OH)CH_3$, $-CH_2CH(OH)C_2H_5$, $-CH_2CH(OH)C_6H_{13}$, $-CH_2CH(OH)C_{10}H_{21}$, $-CH_2CH_2OCH_3$, $-CH_2CH_2OC_2H_5$, $-CH_2CH_2OC_4H_9$, $-(CH_2)_3OH$, $-CH_2CH(OH)CH_2OC_4H_9$, $-CH_2CH(OH)CH_2OC_{12}H_{25}$, $-CH_2CH_2OC_6H_5$, $-CH_2CH_2Cl$, $-CH_2CH(OH)CH_2OC_6H_5$,

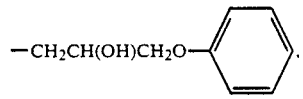

$-CH_2COOH$, $-CH_2CH_2COOH$, $-CH_2COOC_2H_5$, $-CH_2COOC_8H_{17}$, $-CH_2CH_2COOCH_3$, $-CH_2CH_2COOC_4H_9$, $-CH_2CH_2COOC_{12}H_{25}$, $-CH_2CONH_2$, $-CH_2CONHC_4H_9$, $-CH_2CON(C_4H_9)_2$, $-CH_2CH_2CONHC_{12}H_{25}$, $-CH_2CH_2CON(C_2H_5)_2$, $-CH_2CH_2NH_2$, $-CH_2CH_2N(CH_3)_2$, $-(CH_2)_3-NH_2$, $-(CH_2)_3-NHC_4H_9$, $-(CH_2)_3N(CH_3)_2$, $-(CH_2)_3N(C_2H_5)_2$, $-(CH_2)_3NHCOCH_3$, $-(CH_2)_3NHCOC_7H_{15}$, $-CH_2CH_2CN$, $-CH_2CH_2OCOC_3H_7$, $-CH_2CH_2OCOC_{17}H_{35}$, $-CH_2CH(CH_3)-OCOCH_3$, $-CH_2CH(OCOCH_3)CH_2OC_8H_{17}$ or $-CH_2CH(OCOC_7H_{15})CH_2C_6H_5$.

The following groups exemplify alkyl radicals which are interrupted by oxygen:

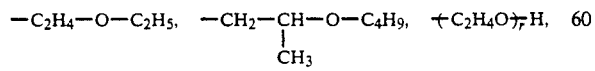

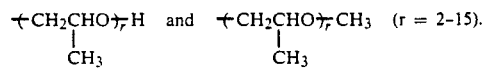

Suitable cycloalkyl radicals in the practice of this invention will typically be cyclopentyl, cyclohexyl, cyclooctyl, cycloundecyl and cyclododecyl.

Preferred compounds of formula (1) are those wherein
R, if n is 1, is alkyl of 1 to 12 carbon atoms, alkyl of 1 to 15 carbon atoms which is substituted by hydroxyl, $-CO_2R_2$ and/or $-O-CO-R_5$; allyl, glycidyl, cyclohexyl, benzyl, $-COR_6$ or $-CH_2CH(OH)CH_2OR_1$,
and $R_1$ is hydrogen, alkyl of 1 to 18 carbon atoms, cyclohexyl or phenyl,
$R_2$ is alkyl of 1 to 12 carbon atoms, alkyl or hydroxyalkyl, each of 3 to 14 carbon atoms and interrupted by oxygen, hydroxyalkyl of 2 to 12 carbon atoms, alkenyl of 3 to 18 carbon atoms, cyclohexyl, glycidyl, benzyl, alkylphenyl containing 1 to 12 carbon atoms in the alkyl moiety, phenyl or furfuryl,
$R_5$ is alkyl of 1 to 6 carbon atoms or alkenyl of 2 to 6 carbon atoms, and
$R_6$ is alkyl of 1 to 12 carbon atoms, alkenyl of 2 to 6 carbon atoms or phenyl, or
R, if n is 2, is alkylene of 2 to 8 carbon atoms, alkylene of 3 to 6 carbon atoms which is interrupted by oxygen, alkenylene of 4 to 8 carbon atoms, xylylene or a radical of formula $-CH_2CH(OH)CH_2-$, $-CH_2CH(OH)CH_2-O-R_{12}-CH_2CH(OH)CH_2-$ or $-(CH_2)_mCO-O-R_{14}-O-CO(CH_2)_m-$, wherein m is 1 or 2,
and $R_{12}$ is alkylene of 2 to 10 carbon atoms, and
$R_{14}$ is alkylene of 2 to 10 carbon atoms or alkylene of 4 to 20 carbon atoms which is interrupted by oxygen.

Among these compounds, those compounds are especially suitable wherein
R, if n is 1, is alkyl of 1 to 8 carbon atoms, alkyl of 1 to 3 carbon atoms which is substituted by $-CO_2R_2$, alkyl of 1 to 12 carbon atoms which is substituted by hydroxyl and/or $-O-CO-R_5$; allyl, glycidyl or $-CH_2CH(OH)CH_2OR_1$, and $R_1$ is hydrogen, alkyl of 1 to 18 carbon atoms, cyclohexyl or phenyl,
$R_2$ is alkyl of 1 to 8 carbon atoms, alkyl of 3 to 12 carbon atoms which is interrupted by oxygen, vinyl, allyl, cyclohexyl, benzyl or glycidyl, and
$R_5$ is alkenyl of 2 to 6 carbon atoms, or
R, if n is 2, is alkylene of 2 to 4 carbon atoms or a radical of formula $-(CH_2)_2CO-O-R_{14}-O-CO(CH_2)_2-$,
and $R_{14}$ is alkylene of 2 to 4 carbon atoms or alkylene of 4 to 12 carbon atoms which is interrupted by oxygen,
and especially those compounds wherein n is 1, and R is alkyl of 1 to 6 carbon atoms or a radical of formula $-CH_2CH(OH)CH_2OR_1$, wherein $R_1$ is hydrogen or alkyl of 1 to 18 carbon atoms, cyclohexyl or phenyl.

A further group of preferred compounds of formula (1) comprises those compounds wherein R, if n is 2, is a radical of formula

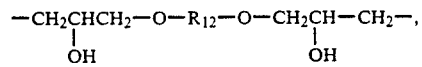

wherein $R_{12}$ is as defined above.

The compounds of formula (1) may conveniently be prepared by reacting the starting compound of formula

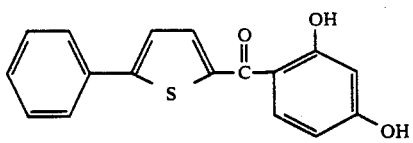

with an appropriate halogen compound of formula

R—X,    (3)

wherein R has the given meaning and X is halogen, preferably chloro or bromo. In this reaction, the compounds of formulae (2) and (3) are dissolved in a suitable solvent, conveniently a ketone, an alcohol or an aromatic solvent, and the solution is heated at elevated temperature in the presence of a base. This coupling reaction can also be carried out if the components are not readily soluble in the chosen solvent and are in the form of a dispersion.

The starting compounds of formula (2) may be obtained by the process described in GB-B-973 919.

Epoxides of formula

wherein $R_1$ has the given meaning, are used to prepare those compounds of formula (1), wherein n is 1, R is R —$CH_2CH(OH)CH_2OR_1$ and $R_1$ is hydrogen, $C_1$-$C_{18}$alkyl, cyclohexyl or phenyl.

Components of formula

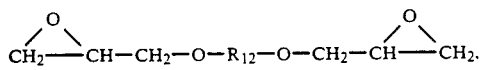

which contain two epoxy groups, wherein $R_{12}$ has the given meaning, are used to prepare those compounds of formula (1), wherein n is 2 and R is

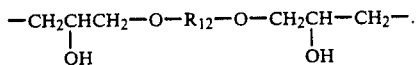

The novel compounds of formula (1) effectively absorb radiation in the range of 300 to 400 nm and hence are suitable for use as UV absorbers. They can be used in particular as UV absorbers in photographic materials, as they readily meet the following criteria:

(1) they do not impair the sensitometric properties of the materials in which they are present, (2) they do not undergo change either on exposure or during processing and in the subsequent storage of the materials, (3) they are stable to UV radiation, heat and moisture.

On account of their yellowish inherent colour, the novel compounds will find utility rather more in film materials than in photographic paper materials. Such materials on the conventional transparent supports disclosed, inter alia, in RESEARCH DISCLOSURE, November 1989, on page 879, may contain light-sensitive layers, antihalo layers, interlayers as well as blocking and protective layers in all known sequences. Examples of materials of this type are disclosed in the above mentioned RESEARCH DISCLOSURE on page 872.

Layers which contain at least one novel compound can be inserted anywhere in the material. Such layers can (except for the binder) be free from further components. However, they may also contain photographically active substances such as silver halide and/or dye couplers. The preferred arrangement is that in which the binder layers containing the UV absorbers are above the topmost silver halide emulsion layer, between two silver halide emulsion layers or on the back of the support.

The appropriate layer will preferably contain the compounds of formula (1) in a coating weight of 5 to 1500 mg/m², most preferably of 5 to 700 mg/m².

The compounds can be incorporated in the appropriate binder in conventional manner using a suitable solvent, conveniently one listed on page 877 of the above mentioned RESEARCH DISCLOSURE, suitable binders being the known binders listed on page 873 of this same publication.

The following Examples illustrate the invention in more detail.

EXAMPLE 1

With stirring, 29.6 g of the compound of formula (2), 14.3 g of butyl glycidyl ether and 2.6 g of ethyltriphenylphosphonium bromide are heated for 1 hour at 130° C. The reaction mixture is taken up in 100 ml of toluene, washed with water and dried. The solvent is then removed under reduced pressure to leave a residue which is recrystallised from ethanol. The compound of formula

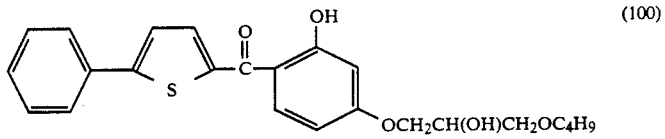

is isolated in a yield of 73% (31.0 g) in the form of yellow crystals with a melting point of 72° C.;

| Elemental analysis: | calcd | 67.58 % C | 6.14 % H | 7.51 % S |
|---|---|---|---|---|
| | found | 67.43 % C | 6.10 % H | 7.80 % S |

In like manner, but using 20.5 g of ethylhexyl glycidyl ether in place of butyl glycidyl ether, the compound of formula

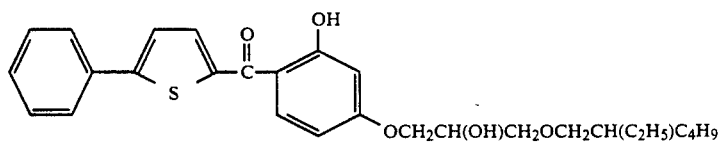

OCH₂CH(OH)CH₂OCH₂CH(C₂H₅)C₄H₉ is obtained in a yield of 71% (34.2 g) with a melting point of 45° C.;

| Elemental analysis: | calcd | 69.68 % C | 7.10 % H | 6.64 % S |
|---|---|---|---|---|
| | found | 69.70 % C | 7.08 % H | 6.3 % S. |

The compounds listed in the following table can be prepared in accordance with the general procedure described in this Example:

TABLE

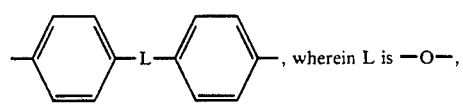

| R | m.p. (°C.) |
|---|---|
| —CH₂CH—CH₂OC₄H₉<br>      |<br>     OH | 72 |
| —CH₂CH—CH₂OCH₂CHC₄H₉<br>      |           |<br>     OH         C₂H₅ | 45 |
| —CH₃ | 112 |
| —CH₂CH=CH₂ | 110 |
| —CH₂—C₆H₅ | 156 |
| —(CH₂)₃CO₂C₂H₅ | 70 |
| —CH₂CO₂CH₂CHC₄H₉<br>             |<br>            C₂H₅ | 86 |
| —C₃H₇ | 103 |
| —C₈H₁₇ | 100 |

EXAMPLE 2

102 mg of UV absorber are dissolved in 2 ml of ethyl acetate. Then 1 ml of this solution is emulsified for 3 minutes by sonication with 9 ml of an aqueous gelatin solution (containing 27.6 g/l of gelatin and 6.8 g/l of an 8% aqueous solution of 4,8-diisobutylnaphthyl-2-sodium sulfonate). Then 4.5 ml of a 0.24% aqueous solution of the sodium salt of 2-hydroxy-4,6-dichloro-1,3,5-triazine are added to 7.5 ml of the above emulsion. 8 ml of this emulsion are then coated on to a polyester support (13×18 cm). The layer contains the UV absorber in a coating weight of 1.09 g/m². After a drying time of 7 days at room temperature, the UV absorption spectrum of the sample is recorded. The spectrum is distinguished by a broad absorption band with a maximum at 372 nm.

What is claimed is:
1. A compound of the formula

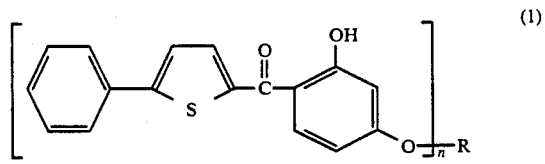

wherein n is 1, 2, 3 or 4, and

R, if n is 1, is alkyl of 1 to 18 carbon atoms which is substituted by —CO₂R₂, or R is —CH₂CH(OH)CH₂OR₁, and R₁ is hydrogen, alkyl of 1 to 18 carbon atoms, cyclohexyl, benzyl, phenyl, tolyl, —CO-alkenyl containing 2 to 4 carbon atoms in the alkenyl moiety or glycidyloxyalkyl containing 3 to 14 carbon atoms in the alkyl moiety, R₂ is alkyl of 1 to 18 carbon atoms, alkyl or hydroxyalkyl, each of 3 to 14 carbon atoms and interrupted by oxygen, hydroxyalkyl of 2 to 18 carbon atoms, alkyl of 1 to 4 carbon atoms which is substituted by glycidyl, cycloalkyl of 5 to 12 carbon atoms, alkenyl of 3 to 18 carbon atoms, benzyl, phenyl, alkylphenyl containing 1 to 12 carbon atoms in the alkyl moiety, furfuryl or a radical of formula —CH₂CH(OH)CH₂OR₁, or R, if n is 2, is a radical of formula —CH₂CH(OH)CH₂—O—R₁₂—O—CH₂CH(OH)CH₂— or —(CH₂)ₘCO—O—R₁₄—O—CO(CH₂)ₘ—, wherein m is 1, 2 or 3, and R₁₂ is alkylene of 2 to 10 carbon atoms, alkylene of 3 to 14 carbon atoms which is interrupted by oxygen, phenylene or a radical of formula

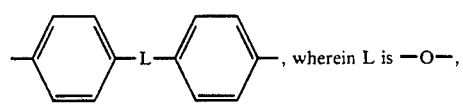, wherein L is —O—,

—S—, —SO₂—, —CH₂— or —C(CH₃)₂—,

R₁₄ is alkylene of 2 to 10 carbon atoms or alkylene of 4 to 30 carbon atoms which is interrupted by oxygen, or R, if n is 3, is a radical of formula

wherein m has the given meaning, and

R₁₅ is alkanetriyl of 3 to 12 carbon atoms, or

R, if n is 4, is a radical of formula

wherein m has the given meaning, and

R₁₆ is alkanetetrayl of 4 to 12 carbon atoms.

2. A compound according to claim 1, wherein

R, if n is 1, is alkyl of 1 to 15 carbon atoms which is substituted by —CO$_2$R$_2$ or —CH$_2$CH(OH)CH$_2$OR$_1$, and R$_1$ is hydrogen, alkyl of 1 to 18 carbon atoms, cyclohexyl or phenyl, R$_2$ is alkyl of 1 to 12 carbon atoms, alkyl or hydroxyalkyl, each of 3 to 14 carbon atoms and interrupted by oxygen, hydroxyalkyl of 2 to 12 carbon atoms, alkenyl of 3 to 18 carbon atoms, cyclohexyl, glycidyl, benzyl, alkylphenyl containing 1 to 12 carbon atoms in the alkyl moiety, phenyl or furfuryl, R, if n is 2, is a radical of formula —CH$_2$CH(OH)CH$_2$—O—R$_{12}$—O—CH$_2$CH(OH)CH$_2$— or —(CH$_2$)$_m$CO—O—R$_{14}$—O—CO(CH$_2$)$_m$—, wherein m is 1 or 2, and R$_{12}$ is alkylene of 2 to 10 carbon atoms, and R$_{14}$ is alkylene of 2 to 10 carbon atoms or alkylene of 4 to 20 carbon atoms which is interrupted by oxygen.

3. A compound according to claim 1, wherein

R, if n is 1, is alkyl of 1 to 3 carbon atoms which is substituted by —CO$_2$R$_2$ or —CH$_2$CH(OH)CH$_2$OR$_1$, and R$_1$ is hydrogen, alkyl of 1 to 18 carbon atoms, cyclohexyl or phenyl, R$_2$ is alkyl of 1 to 8 carbon atoms, alkyl of 3 to 12 carbon atoms which is interrupted by oxygen, vinyl, allyl, cyclohexyl, benzyl or glycidyl, and R, if n is 2, is a radical of formula

—(CH$_2$)$_2$CO—O—R$_{14}$—O—CO(CH$_2$)$_2$—, and R$_{14}$ is alkylene of 2 to 4 carbon atoms or alkylene of 4 to 12 carbon atoms which is interrupted by oxygen.

4. A compound according to claim 1, wherein n is 1 and R is a radical of formula —CH$_2$CH(OH)CH$_2$OR$_1$, wherein R$_1$ is hydrogen or alkyl of 1 to 18 carbon atoms, cyclohexyl or phenyl.

5. A compound according to claim 1, wherein R, if n is 2, is a radical of formula $$-CH_2\underset{OH}{CH}CH_2-O-R_{12}-O-CH_2\underset{OH}{CH}-CH_2-,$$

wherein R$_{12}$ is as defined in claim 1.

* * * * *